(12) United States Patent
Patel et al.

(10) Patent No.: US 12,042,538 B2
(45) Date of Patent: *Jul. 23, 2024

(54) METHODS OF REDUCING PARTICLE FORMATION AND COMPOSITIONS FORMED THEREBY

(71) Applicant: Regeneron Pharmaceuticals, Inc., Tarrytown, NY (US)

(72) Inventors: Mayank Patel, New City, NY (US); Stacy Wasinger, Hopewell Junction, NY (US); Danya Spritzer, Briarcliff Manor, NY (US); Xiaolin Tang, Old Tappan, NJ (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 244 days.

This patent is subject to a terminal disclaimer.

(21) Appl. No.: 16/100,369

(22) Filed: Aug. 10, 2018

(65) Prior Publication Data

US 2019/0083618 A1 Mar. 21, 2019

Related U.S. Application Data

(60) Provisional application No. 62/560,365, filed on Sep. 19, 2017.

(51) Int. Cl.
| | | |
|---|---|---|
| A61K 39/395 | (2006.01) | |
| A61K 38/46 | (2006.01) | |
| A61K 47/26 | (2006.01) | |
| C07K 16/00 | (2006.01) | |
| A61K 9/00 | (2006.01) | |

(52) U.S. Cl.
CPC ...... *A61K 39/39591* (2013.01); *A61K 38/465* (2013.01); *A61K 47/26* (2013.01); *C07K 16/00* (2013.01); *A61K 9/0019* (2013.01)

(58) Field of Classification Search
None
See application file for complete search history.

(56) References Cited

U.S. PATENT DOCUMENTS

| | | |
|---|---|---|
| 4,801,726 A | 1/1989 | Giese et al. |
| 4,937,188 A | 6/1990 | Giese et al. |
| 5,190,864 A | 3/1993 | Giese et al. |
| 5,412,083 A | 5/1995 | Giese et al. |
| 5,641,870 A | 6/1997 | Rinderknecht et al. |
| 6,066,719 A | 5/2000 | Zapata |
| 6,214,984 B1 | 4/2001 | Zapata |
| 6,441,160 B2 | 8/2002 | Kitamura et al. |
| 7,038,017 B2 | 5/2006 | Rinderknecht et al. |
| 7,070,959 B1 | 7/2006 | Papadopoulos et al. |
| 7,101,982 B2 | 9/2006 | Ghose et al. |
| 7,220,356 B2 | 5/2007 | Thommes et al. |
| 7,303,746 B2 | 12/2007 | Wiegand et al. |
| 7,303,747 B2 | 12/2007 | Wiegand et al. |
| 7,306,799 B2 | 12/2007 | Wiegand et al. |
| RE40,070 E | 2/2008 | Shadle et al. |
| 7,374,757 B2 | 5/2008 | Papadopoulos et al. |
| 7,374,758 B2 | 5/2008 | Papadopoulos et al. |
| 7,385,040 B2 | 6/2008 | Johansson et al. |
| 7,393,631 B2 | 7/2008 | Cannon-Carlson et al. |
| 7,427,659 B2 | 9/2008 | Shukla et al. |
| 7,531,173 B2 | 5/2009 | Wiegand et al. |
| 7,608,261 B2 | 10/2009 | Furfine et al. |
| 7,666,413 B2 | 2/2010 | Liu et al. |
| 7,700,097 B2 | 4/2010 | Braslawsky et al. |
| 7,714,112 B2 | 5/2010 | Engstrand et al. |
| 7,750,129 B2 | 7/2010 | Johansson et al. |
| RE41,555 E | 8/2010 | Shadle et al. |
| RE41,595 E | 8/2010 | Shandle et al. |
| 7,795,405 B2 | 9/2010 | DiNovo |
| 7,863,426 B2 | 1/2011 | Wan et al. |
| 7,972,598 B2 | 7/2011 | Daly et al. |
| 8,003,364 B2 | 8/2011 | Post Hansen et al. |
| 8,012,754 B2 | 9/2011 | Rinderknecht et al. |
| 8,029,791 B2 | 10/2011 | Papadopoulos et al. |
| 8,084,032 B2 | 12/2011 | Yumioka et al. |
| 8,092,803 B2 | 1/2012 | Furfine et al. |
| 8,163,531 B2 | 4/2012 | Post Hansen et al. |
| 8,231,876 B2 | 7/2012 | Wan et al. |
| 8,343,349 B2 | 1/2013 | Eriksson et al. |
| 8,343,737 B2 | 1/2013 | Papadopoulos et al. |
| 8,410,928 B2 | 4/2013 | Ganguly et al. |
| 8,435,527 B2 | 5/2013 | Yumioka et al. |

(Continued)

FOREIGN PATENT DOCUMENTS

| | | |
|---|---|---|
| EP | 1 475 100 A1 | 11/2004 |
| WO | 9625425 A1 | 8/1996 |

(Continued)

OTHER PUBLICATIONS

Sing et al., AAPS PharmSciTech, vol. 13 (2) p. 422-430, 2012.*
Hanania et al., "Lebrikizumab in moderate-to-severe asthma: pooled data from two randomized placebo-controlled studies" downloaded from http://thorax.bmj.com/ on Jul. 14, 2017,—published by group.bmj.com (10 pages).
Song, "ChP Monograph: Polysorbate 80 (PS 80) for injectable Product," PS 80 Workshop with Chinese Pharmacopeia Commission (CPC) Apr. 26, 2017 (12 pages).
0 et al., "Overlooking Subvisible Particles in Therapeutic Protein Products: Gapes That May Compromise Product Quality" published online Aug. 14, 2008 in Wiley InterScience (www.interscience.wiley.com). DOI 10.1002/jps.21530 (5 pages).

(Continued)

*Primary Examiner* — Yunsoo Kim
(74) *Attorney, Agent, or Firm* — Bookoff McAndrews, PLLC

(57) ABSTRACT

Biopharmaceutical compositions and drug products disclosed herein exhibit reduced amounts of subvisible particle formation. Compositions and drug products disclosed herein comprise a protein and a surfactant or stabilizer including high percentage amounts (e.g., at least 97%) of a long-chain fatty acid ester. Also disclosed herein are methods of preparing and storing such compositions and drug products.

21 Claims, 4 Drawing Sheets
Specification includes a Sequence Listing.

(56) References Cited

U.S. PATENT DOCUMENTS

| | | | |
|---|---|---|---|
| 8,470,328 B2 | 6/2013 | Yumioka et al. |
| 8,470,578 B2 | 6/2013 | Post Hansen et al. |
| 8,491,904 B2 | 7/2013 | Hickman |
| 8,568,586 B2 | 10/2013 | Cunnien et al. |
| 8,603,473 B2 | 12/2013 | Glaser et al. |
| 8,608,960 B2 | 12/2013 | Thommes et al. |
| 8,647,842 B2 | 2/2014 | Papadopoulos et al. |
| 8,821,865 B2 | 9/2014 | Neu et al. |
| 8,821,879 B2 | 9/2014 | Babuka et al. |
| 8,840,884 B2 | 9/2014 | Kakuta et al. |
| 8,871,209 B2 | 10/2014 | Stitt et al. |
| 8,895,709 B2 | 11/2014 | Hickman et al. |
| 8,895,710 B2 | 11/2014 | Engstrand et al. |
| 8,946,395 B1 | 2/2015 | Hierigstad et al. |
| 8,969,532 B2 | 3/2015 | DeFrees et al. |
| 9,017,687 B1 | 4/2015 | Wang et al. |
| 9,018,361 B2 | 4/2015 | Hickman et al. |
| 9,051,384 B2 | 6/2015 | Kakuta et al. |
| 9,067,990 B2 | 6/2015 | Wang et al. |
| 9,102,723 B2 | 8/2015 | Wan et al. |
| 9,109,010 B2 | 8/2015 | Hickman et al. |
| 9,109,201 B2 | 8/2015 | Post Hansen et al. |
| 9,150,645 B2 | 10/2015 | Subramanian et al. |
| 9,150,938 B2 | 10/2015 | Oroskar |
| 9,181,572 B2 | 11/2015 | Subramanian et al. |
| 9,193,787 B2 | 11/2015 | Chumsae |
| 9,249,182 B2 | 2/2016 | Herigstad |
| 9,266,950 B2 | 2/2016 | Hickman |
| 9,334,319 B2 | 5/2016 | Ramasubramanyan et al. |
| 9,346,879 B2 | 5/2016 | Ramasubramanyan et al. |
| 9,359,434 B2 | 6/2016 | Subramanian et al. |
| 9,488,625 B2 | 11/2016 | Felgenhauer et al. |
| 9,505,833 B2 | 11/2016 | Chumsae |
| 9,518,082 B2 | 12/2016 | Allison et al. |
| 9,650,411 B2 | 5/2017 | Ishihara |
| 9,650,412 B2 | 5/2017 | Konstantinov et al. |
| 9,650,413 B2 | 5/2017 | Konstantinov et al. |
| 9,657,056 B2 | 5/2017 | Konstantinov et al. |
| 9,683,012 B2 | 6/2017 | Yoon et al. |
| 9,683,033 B2 | 6/2017 | Subramanian et al. |
| 9,688,752 B2 | 6/2017 | Wang et al. |
| 9,708,365 B2 | 7/2017 | Mendiratta et al. |
| 9,708,399 B2 | 7/2017 | Wang et al. |
| 9,708,400 B2 | 7/2017 | Subramanian et al. |
| 9,766,217 B2 | 9/2017 | Kidal et al. |
| 9,878,266 B2 | 1/2018 | Engstrand et al. |
| 9,920,120 B2 | 3/2018 | Yu et al. |
| 9,945,858 B2 | 4/2018 | Gunawan et al. |
| 9,957,318 B2 | 5/2018 | Ramasubramanyan et al. |
| 9,975,948 B2 | 5/2018 | Hickman |
| 9,994,609 B2 | 6/2018 | Ghose et al. |
| 10,017,746 B2 | 7/2018 | Sheldon et al. |
| 10,023,608 B1 | 7/2018 | Ma et al. |
| 10,053,489 B2 | 8/2018 | Kim et al. |
| 10,115,576 B2 | 10/2018 | Geromanos et al. |
| 10,188,732 B2 | 1/2019 | Conley et al. |
| 10,342,876 B2 * | 7/2019 | Bak ................. A61K 39/39591 |
| 10,363,496 B2 | 7/2019 | Coutard |
| 10,494,429 B2 | 12/2019 | Yu et al. |
| 10,533,045 B2 | 1/2020 | Allison et al. |
| 10,597,443 B2 | 3/2020 | Schurpf et al. |
| 10,597,446 B2 | 3/2020 | Yu et al. |
| 10,597,447 B2 | 3/2020 | Yu et al. |
| 10,626,376 B2 | 4/2020 | McNally et al. |
| 10,692,709 B2 | 6/2020 | Geromanos et al. |
| 10,696,735 B2 | 6/2020 | Yonan et al. |
| 10,696,952 B2 | 6/2020 | Sheldon et al. |
| 10,702,603 B2 | 7/2020 | Conley et al. |
| 10,788,494 B2 | 9/2020 | Gunawan et al. |
| 10,822,404 B2 | 11/2020 | Yu et al. |
| 10,894,079 B2 | 1/2021 | Mullner et al. |
| 10,940,401 B2 | 3/2021 | Mahajan et al. |
| 10,947,262 B2 | 3/2021 | Gronke et al. |
| 2002/0064860 A1 | 5/2002 | Cannon-Carlson et al. |
| 2004/0106184 A1 | 6/2004 | Senesac |
| 2005/0163782 A1 | 7/2005 | Glaser et al. |
| 2005/0214278 A1 | 9/2005 | Kakuta et al. |
| 2006/0027454 A1 | 2/2006 | DiNovo |
| 2006/0257972 A1 | 11/2006 | Ishihara |
| 2007/0213513 A1 | 9/2007 | Van Alstine et al. |
| 2008/0299545 A1 | 12/2008 | Zhang et al. |
| 2008/0299671 A1 | 12/2008 | Glad et al. |
| 2010/0035299 A1 | 2/2010 | DeFrees et al. |
| 2010/0069617 A1 | 3/2010 | Gagnon |
| 2010/0127860 A1 | 5/2010 | Ganguly et al. |
| 2010/0136025 A1 | 6/2010 | Hickman et al. |
| 2010/0278822 A1 | 11/2010 | Fraunhofer et al. |
| 2011/0147312 A1 | 6/2011 | Cunnien et al. |
| 2013/0131318 A1 | 5/2013 | Kremer et al. |
| 2013/0149310 A1 | 6/2013 | Jasson et al. |
| 2013/0336957 A1 | 12/2013 | Wang et al. |
| 2014/0010820 A1 | 1/2014 | Wang et al. |
| 2014/0046038 A1 | 2/2014 | Ishihara |
| 2014/0072585 A1 | 3/2014 | Herigstad et al. |
| 2014/0154270 A1 | 6/2014 | Wang et al. |
| 2014/0302053 A1 | 10/2014 | Huang et al. |
| 2014/0356370 A1 | 12/2014 | Swergold et al. |
| 2014/0356371 A1 | 12/2014 | Swergold et al. |
| 2014/0356372 A1 | 12/2014 | Stahl et al. |
| 2015/0170892 A1 | 6/2015 | Geromanos et al. |
| 2015/0210735 A1 | 7/2015 | Hickman et al. |
| 2015/0299249 A1 | 10/2015 | Herigstad et al. |
| 2015/0337029 A1 | 11/2015 | Kyratsous et al. |
| 2016/0011181 A1 | 1/2016 | Takahashi et al. |
| 2016/0083452 A1 | 3/2016 | Hickman et al. |
| 2016/0101181 A1 | 4/2016 | Bak et al. |
| 2016/0115193 A1 | 4/2016 | Herigstad et al. |
| 2016/0152717 A1 | 6/2016 | Cao et al. |
| 2016/0215040 A1 | 7/2016 | Kyratsous et al. |
| 2016/0251441 A1 | 9/2016 | O'Connor et al. |
| 2016/0319012 A1 | 11/2016 | Yu et al. |
| 2016/0320391 A1 | 11/2016 | Gunawan et al. |
| 2017/0101472 A1 | 4/2017 | Ullman et al. |
| 2017/0158760 A1 | 6/2017 | Hickman et al. |
| 2017/0174779 A1 | 6/2017 | Varghese et al. |
| 2017/0174781 A1 | 6/2017 | Brownstein |
| 2017/0342145 A1 | 11/2017 | Wang et al. |
| 2017/0349654 A1 | 12/2017 | Wang et al. |
| 2018/0222938 A1 | 8/2018 | Herigstad et al. |
| 2018/0230210 A1 | 8/2018 | Hickman |
| 2019/0062419 A1 | 2/2019 | Ramasubramanyan et al. |
| 2019/0144495 A1 | 5/2019 | Ghose et al. |
| 2019/0248823 A1 | 8/2019 | Gronke et al. |
| 2019/0298829 A1 | 10/2019 | Wan et al. |
| 2020/0002373 A1 | 1/2020 | Livigini et al. |
| 2020/0223913 A1 | 7/2020 | Allison et al. |
| 2021/0009632 A1 | 1/2021 | Tan et al. |
| 2021/0010055 A1 | 1/2021 | Cura et al. |

FOREIGN PATENT DOCUMENTS

| | | |
|---|---|---|
| WO | WO 2007110339 A1 | 10/2007 |
| WO | WO 2009058769 A1 | 5/2009 |
| WO | 2010019814 A1 | 2/2010 |
| WO | 2011028961 A2 | 3/2011 |
| WO | WO 2011098526 A1 | 8/2011 |
| WO | 2011112669 A1 | 9/2011 |
| WO | WO 2012030512 A1 | 3/2012 |
| WO | WO 2012065072 A2 | 5/2012 |
| WO | WO 2013066707 A1 | 5/2013 |
| WO | WO 2013078170 A1 | 5/2013 |
| WO | WO 2013176754 A1 | 11/2013 |
| WO | WO 2013177115 A2 | 11/2013 |
| WO | WO 2013177118 A2 | 11/2013 |
| WO | WO 2014100143 A2 | 6/2014 |
| WO | WO 2014143185 A1 | 9/2014 |
| WO | WO 2014145208 A1 | 9/2014 |
| WO | 2014158231 A1 | 10/2014 |
| WO | 2015035180 A1 | 3/2015 |
| WO | WO 2015038888 A1 | 3/2015 |
| WO | WO 2016057739 A1 | 4/2016 |
| WO | 2017140881 A1 | 8/2017 |
| WO | 2018027195 A1 | 2/2018 |
| WO | 2019040671 A1 | 2/2019 |

(56) References Cited

FOREIGN PATENT DOCUMENTS

| | | | |
|---|---|---|---|
| WO | 2019178495 | A1 | 9/2019 |
| WO | 2019246153 | A1 | 12/2019 |
| WO | 2020023566 | A1 | 1/2020 |
| WO | 2020037016 | A1 | 2/2020 |
| WO | 2020096958 | A1 | 5/2020 |
| WO | 2020172658 | A1 | 8/2020 |
| WO | 2020205469 | A1 | 10/2020 |
| WO | 2020264411 | A1 | 12/2020 |

OTHER PUBLICATIONS

Doshi et al., "Understanding Particle Formation: Solubility of Free Fatty Acids as Polysorbate 20 Degradation Byproducts in Therapeutic Monoclonal Antibody Formulations," Mol. Pharmaceutics 2015, 12, 3792-3804, 2015 American Chemical Society, DOI: 10.1021/acs.molpharmaceut.5b00310 (13 pages).

Narhi et al., "Subvisible (1-100 um) Particle Analysis During Biotherapeutic Drug Product Development: Part 1, Considerations and Strategy" published online Apr. 1, 2015 I Wiley Online Library (wileyonlinelibrary.com). DOI 10.1002/jps.24437 Journal of Pharacuetical Sciences pp. 1899-1908 (10 pages).

Joucla et al., J Chromatography B, (2013) vols. 942-943; pp. 126-133.

Mihara et al., Journal of Pharmaceutical Sciences, (2015) 104:3991-3996.

Valente et al., Biotechnology and Bioengineering, 112: 12302-1242 doi: 10.1002/bit.25515 (First published online Jan. 16, 2015).

Kishore et al., "The Degradation of Polysorbates 20 and 80 and its potential Impact on the Stability of Biotherapeutics," Pharm. Res. 28: 1194-1210 (2011).

"GE Healthcare Life Sciences Hydrophobic Interaction Chromatography (HIC) Selection Guide," Jun. 2012, retrieved on Mar. 7, 2016 from http://www.gelifesciences.com/gehcls_images/GELS/Related%20Content/Files/1349939730181/ litdoc29022223_20130925000229.pdf.

International Search Report & Written Opinion of the International Searching Authority for International application No. PCT/US2015/054600, dated Dec. 16, 2015.

Akoh et al., "GDSL family of serine esterases/lipases," Progress in Lipid Research 43 (2004) 534-552.

Gassama-Dauge, et al. "Substrate Specificity of Phospholipase B from Guinea Pig Intestine—1\ glycerol ester lipase with broad specificity," J. Biol. Chem. Issue of Jul. 5, 1992, 267(19), pp. 13418-13424.

Hogwood et al., "Measurement and control of host cell proteins (HCPs) in CHO cell bioprocesses," Curr. Opin. Biotechnol. 30:153-160 (2014).

Jensen et al., "Biochemical characterization and liposomal localization localization of the mannose-6-phosphate protein p76," Biochem. J. 402:449-458 (2007).

Kishore, R. K., Degradation of Polysorbates 20 and 80: Studies on Thermal Autoxidation and Hydrolysis:, J. Pharmacol. Sci., 100(2):721-31 (2011), Published online on Aug. 27, 2010 in Wiley Online Library.

Kuczewski et al., "Development of a polishing step using a hydrophobic interaction membrane adsorber with a Per. C6®—derived recombinant antibody," Biotech. Bioeng. 105(2):296-305 (2010).

LaBrenz, "Ester hydrolysis of polysorbate 80 in mAb drug product: evidence in support of the hypothesized risk after observation of visible particulate in mAb formulations," J. Pharma. Sci. 103(8):2268-77 (2014).

Li et al., "Characterization and stability study of polysorbate 20 in therapeutic monoclonal antibody formulation by multidimensional ultrahigh-performance liquid chromatography-charged aerosol detection-mass spectrometry," Anal Chem. May 2, 20140;86(10):5150-7.

Morgan et al., "Identification of phospholipase B from Dictyostelium discoideum reveals a new lipase family present in mammals, flies and nematodes, but not yeast," Biochem. J. 382: 441-449 (2004).

Müller and Franzreb, "Suitability of commercial hydrophobic interaction sorbents for temperature controlled protein liquid chromatography under low salt conditions," J. Chroma. A 1260:88-96 (2012).

Narhi et al., "A critical review of analytical methods for subvisible and visible particles," Curr Pharm Biotechnol 10(4):373-381 (2009).

Repo et al., "Is the bovine lysosomal phospholipase B-like protein an amidase?" Proteins, 82:300-311 (2014), Published online Aug. 12, 2013 in Wiley Online Library.

Roettger and Ladisch, "Hydrophobic interaction chromatography," Biotechnol Adv. 7(1):15-29 (1989).

Saggu et al., "Identification of Subvisible Particles in Biopharmaceutical Formulations Using Raman Spectroscopy Provides Insight into Polysorbate 20 Degradation Pathway," Pharm Res. Sep. 2015;32(9):2877-88.

Sharma et al., "Micro-flow imaging: Flow microscopy applied to sub-visible particulate analysis in protein formulations," AAPS J. 12(3): 455-464 (2010).

Singh et al., "An industry perspective on the monitoring of subvisible particles as a quality attribute for protein therapeutics," J. Pharma. Sci. 99(8):3302-21 (2010).

Singh and Toler, "Monitoring of subvisible particles in therapeutic proteins," Methods Mol Biol. (2012); 899:379-401.

Singh et al., Clarification of Recombinant Proteins From High Cell Density Mammalian Cell Culture Systems Using New Improved Depth Filters Biotechnol. Bioeng., vol. 110(7):1964-1972 (2013).

Siska et al., "Free fatty acid particles in protein formulations, part 2: Contribution of polysorbate raw material," J. Pharma. Sci. 104(2):447-56 (Epub Sep. 5, 2014).

Tait, A. S., et al., "Differential Response in Downstream Processing of CHO Cells Grown Under Mild Hypothermic Conditions" Chemical Engineers Biotechnol. Prog., 29:688-696 (2013).

Wilton, David C. and Waite, Moseley, Biochemistry Lipids, Lipoproteins and Membranes (4th Edn.), D.E. Vance and J.E. Vance (Eds.) Chapter 11: Phospholipases, pp. 291-314 (2002).

Vanderlaan, M., "Recent experiences with Host Cell Protein Impurity Analysis," CaSSS Conference (proceedings), Nov. 13, 2014.

Vanderlaan et al., "Hamster Phospholipase B-Like 2 (PLBL2): A Host-Cell Protein Impurity in Therapeutic Monoclonal Antibodies Derived from Chinese Hamster Ovary Cells," Bioprocess International 2015.

Yuk et al., "More similar than different: Host cell protein production using three null CHO cell lines," Biotechnol Bioeng. Oct. 2015;112(10):2068-83.

Zhang et al., "Comprehensive tracking of host cell proteins during monoclonal antibody purifications using mass spectrometry" mAbs 6(3):659-670; (May/Jun. 2014).

Zölls et al., "How Subvisible Particles Become Invisible—Relevance of the Refractive Index for Protein Particle Analysis," J. Pharm. Sci., DOI 10.1002/jps.23479, received Oct. 29, 2012, accepted Jan. 31, 2013, published online in Wiley Online Library (13 pages).

Cao et al., "Free Fatty Acid Particles in Protein Formulations, Part 1: Microspectroscopic Identification," Pharmaceutical Biotechnology, DOI 10.1002/jps.24126, received Jun. 4, 2014, accepted Jul. 30, 2014, published online in Wiley Online Library (14 pages).

Jones et al., "Considerations for the Use of Polysorbates in Biopharmaceuticals," Pharm. Res. (2018) 35:148, published online May 24, 2018 (8 pages).

Kerwin, "Polysorbates 20 and 80 Used in the Formulation of Protein Biotherapeutics: Structure and Degradation Pathways," Journal of Pharmaceutical Sciences, vol. 97, No. 8, 2924-2935, Aug. 2008, DOI 10.1002/jps.21190 (12 pages).

Martos et al., "Trends on Analytical Characterization of Polysorbates and Their Degradation Products in Biopharmaceutical Formulations," Journal of Phamaceutical Sciences 106 (2017) 1722-1735, Mar. 14, 2017 (14 pages).

International Search Report and Written Opinion for PCT/US2018/046183, dated Oct. 25, 2018 (16 pages).

Dixit, et al., "Residual Host Cell Protein Promotes Polysorbate 20 Degradation in a Sulfatase Drug Product Leading to Free Fatty Acid Particles," Journal of Pharmaceutical Sciences, vol. 105, pp. 1657-1666 (2016).

(56) References Cited

OTHER PUBLICATIONS

Ilko et al., "Fatty acid composition analysis in polysorbate 80 with high performance liquid chromatography coupled to charged aerosol detection", European Journal of Pharmaceutics and Biopharmaceutics, vol. 94, pp. 569-574, Aug. 2015.

* cited by examiner

METHODS OF REDUCING PARTICLE FORMATION AND COMPOSITIONS FORMED THEREBY

CROSS-REFERENCE TO RELATED APPLICATIONS

This application claims the benefit of priority from U.S. Provisional Application No. 62/560,365, filed on Sep. 19, 2017, the entirety of which is incorporated herein by reference.

SEQUENCE LISTING

This application contains a sequence listing, submitted electronically in ASCII format under the filename 00166-0011-01000_Sequence_Listing.txt, which is incorporated by reference herein in its entirety. The ASCII copy of the sequence listing was created on August 9, 2018, and is 6,904 bytes in size.

FIELD OF THE DISCLOSURE

This disclosure is directed to biopharmaceutical formulations and drug products exhibiting reduced amounts of subvisible particle formation upon storage, and to methods of their preparation and storage. Specifically, this disclosure is directed to formulations and drug products comprising a protein and a surfactant or stabilizer including high percentage amounts of a long-chain, mono-unsaturated fatty acid ester, and methods of their preparation and storage.

BACKGROUND

Polysorbates have conventionally been used in drug products (also referred to as "DP") containing a protein as an active ingredient, to protect proteins from surface-induced (air/liquid or solid/liquid) instability during manufacturing, storage, handling, and administration. It has been discovered that lipases copurified with proteins of interest (POIs), when present in formulations with polysorbates, may hydrolyze the fatty acid esters in polysorbates into free fatty acids. Non-enzymatic hydrolysis of fatty acid esters in polysorbates may also occur in formulations at a slower rate. The free fatty acids formed as a result of hydrolysis may aggregate and form particulates in drug products containing such formulations over time. Particulates (both visible and subvisible) can impact product stability, reduce a drug product's shelf life because of its failure to meet compendial particulate matter specifications (e.g., U.S. FDA specifications), and may have clinical effects, such as an immunogenic reaction upon administration.

Hydrophobic interaction chromatography (HIC) or affinity chromatography of POIs may reduce or remove lipases that are co-purified with the POIs, thus decreasing hydrolysis of fatty acid esters. However, addition of a HIC or affinity chromatography step to the preparation of protein formulations requires adding, for example, equipment, materials, preparation, protocol, and protocol validation to manufacturing methods, which results in added time and costs. In addition, a HIC or affinity chromatography step to remove enzymes will not aid in preventing non-enzymatic hydrolysis of fatty acid esters in formulations. A method of reducing or preventing subvisible and visible particulate formation in protein compositions, for example, without the use of added HIC or affinity chromatography steps, is therefore desired.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments. Any features of an embodiment or example described herein (e.g., composition, formulation, method, etc.) may be combined with any other embodiment or example, and are encompassed by the present disclosure.

Figure 1:
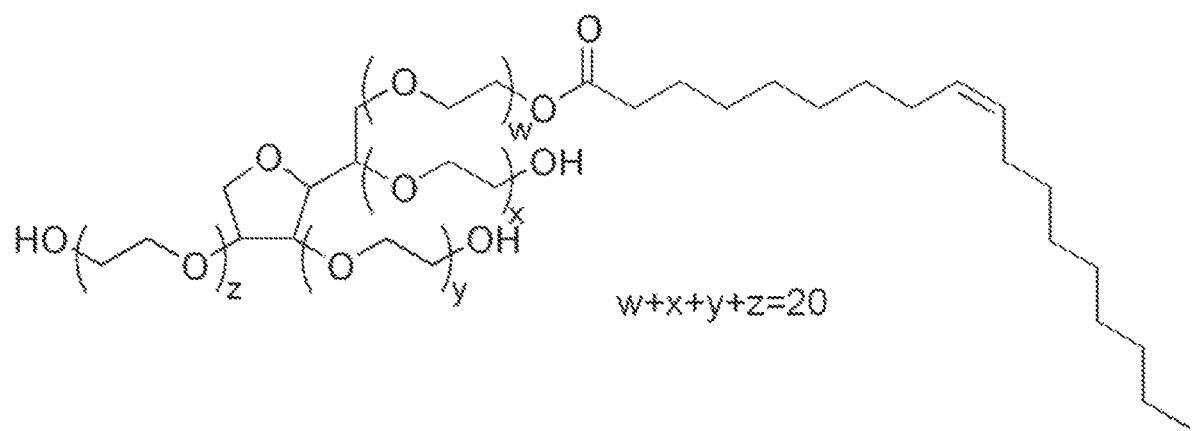
FIG. 1 is a diagram of the chemical structure of polyoxyethylene (20) sorbitan monooleate, the predominant fatty acid ester in polysorbate 80.

As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." For the terms "for example" and "such as," and grammatical equivalences thereof, the phrase "and without limitation" is understood to follow unless explicitly stated otherwise.

As used herein, the term "about" is meant to account for variations due to experimental error. All measurements reported herein are understood to be modified by the term "about," whether or not the term is explicitly used, unless explicitly stated otherwise. As used herein, the singular forms "a," "an," and "the" include plural referents unless the context clearly dictates otherwise.

It should be noted that all numeric values disclosed herein (including all disclosed values, limits, and ranges) may have a variation of +/−10% (unless a different variation is specified) from the disclosed numeric value. Moreover, in the claims, values, limits, and/or ranges means the value, limit, and/or range +/−10%.

DETAILED DESCRIPTION

This disclosure is not limited to the particular compositions, formulations, material manufacturer, drug products, methods, or experimental conditions disclosed herein, as many variations are possible within the purview of one of ordinary skill in the art. The terminology used herein is for the purpose of describing particular embodiments only, and is not intended to be limiting.

Unless defined otherwise, all technical and scientific terms used herein have the same meaning as is commonly understood by one of ordinary skill in the art to which this disclosure belongs. Although any methods and materials similar or equivalent to those described herein can be used in the practice or testing of the present invention, particular methods and materials are now described. All publications mentioned are hereby incorporated by reference.

The term "protein" as used herein refers to any amino acid polymer having more than about 20 amino acids covalently linked via amide bonds. Proteins contain one or more amino acid polymer chains, generally known in the art as "polypeptides." Thus, a polypeptide may be a protein, and a protein may contain multiple polypeptides to form a single functioning biomolecule of a single conformation. Disulfide bridges (e.g., between cysteine residues to form cystine) may be present in some proteins. For example, disulfide bridges are essential to proper structure and function of insulin, immunoglobulins, protamine, and the like.

In addition to disulfide bond formation, proteins may be subject to other post-translational modifications. Those modifications include lipidation (e.g., myristoylation, palmitoylation, farnesoylation, geranylgeranylation, and glycosylphosphatidylinositol (GPI) anchor formation), alkylation (e.g., methylation), acylation, amidation, glycosylation (e.g., addition of glycosyl groups at arginine, asparagine, cysteine, hydroxylysine, serine, threonine, tyrosine, and/or tryptophan), and phosphorylation (i.e., the addition of a phosphate group to serine, threonine, tyrosine, and/or histidine).

As used herein, the term "protein" includes biotherapeutic proteins, recombinant proteins used in research or therapy, trap proteins and other Fc-fusion proteins, chimeric proteins, antibodies, monoclonal antibodies, human antibodies, bispecific antibodies, antibody fragments, antibody-like molecules, nanobodies, recombinant antibody chimeras, cytokines, chemokines, peptide hormones, and the like. Proteins may be produced using recombinant cell-based production systems, such as the insect bacculovirus system, yeast systems (e.g., *Pichia* sp.), mammalian systems (e.g., CHO cells and CHO derivatives like CHO-K1 cells).

The term "antibody," as used herein, includes immunoglobulins comprised of four polypeptide chains, two heavy (H) chains and two light (L) chains inter-connected by disulfide bonds. Typically, antibodies according to the present disclosure have a molecular weight of over 100 kDa, such as between 130 kDa and 200 kDa, such as about 140 kDa, 145 kDa, 150 kDa, 155 kDa, or 160 kDa. Each heavy chain comprises a heavy chain variable region (abbreviated herein as HCVR or VH) and a heavy chain constant region. The heavy chain constant region comprises three domains, CH1 CH2 and CH3. Each light chain comprises a light chain variable region (abbreviated herein as LCVR or VL) and a light chain constant region. The light chain constant region comprises one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4 (heavy chain CDRs may be abbreviated as HCDR1, HCDR2 and HCDR3; light chain CDRs may be abbreviated as LCDR1, LCDR2 and LCDR3.

A class of immunoglobulins called Immunoglobulin G (IgG), for example, is common in human serum and comprises four polypeptide chains—two light chains and two heavy chains. Each light chain is linked to one heavy chain via a cystine disulfide bond, and the two heavy chains are bound to each other via two cystine disulfide bonds. Other classes of human immunoglobulins include IgA, IgM, IgD, and IgE. In the case of IgG, four subclasses exist: IgG 1, IgG 2, IgG 3, and IgG 4. Each subclass differs in their constant regions, and as a result, may have different effector functions.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

The term "human antibody," as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The phrase "Fc-containing protein" includes antibodies, bispecific antibodies, immunoadhesins, and other binding proteins that comprise at least a functional portion of an immunoglobulin CH2 and CH3 region. A "functional portion" refers to a CH2 and CH3 region that can bind a Fc receptor (e.g., an FcγR; or an FcRn, i.e., a neonatal Fc receptor), and/or that can participate in the activation of complement. If the CH2 and CH3 region contains deletions, substitutions, and/or insertions or other modifications that render it unable to bind any Fc receptor and also unable to activate complement, the CH2 and CH3 region is not functional.

Fc-containing proteins can comprise modifications in immunoglobulin domains, including where the modifications affect one or more effector function of the binding protein (e.g., modifications that affect FcγR binding, FcRn binding and thus half-life, and/or CDC activity). Such modifications include, but are not limited to, the following modifications and combinations thereof, with reference to EU numbering of an immunoglobulin constant region: 238, 239, 248, 249, 250, 252, 254, 255, 256, 258, 265, 267, 268, 269, 270, 272, 276, 278, 280, 283, 285, 286, 289, 290, 292, 293, 294, 295, 296, 297, 298, 301, 303, 305, 307, 308, 309, 311, 312, 315, 318, 320, 322, 324, 326, 327, 328, 329, 330, 331, 332, 333, 334, 335, 337, 338, 339, 340, 342, 344, 356, 358, 359, 360, 361, 362, 373, 375, 376, 378, 380, 382, 383, 384, 386, 388, 389, 398, 414, 416, 419, 428, 430, 433, 434, 435, 437, 438, and 439.

For example, and not by way of limitation, the binding protein may be an Fc-containing protein and may exhibit enhanced serum half-life (as compared with the same Fc-containing protein without the recited modification(s)), and may have a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at 428 and/or 433 (e.g., L/R/SI/P/Q or K) and/or 434 (e.g., H/F or Y); or a modification at 250 and/or 428; or a modification at 307 or 308 (e.g., 308F, V308F), and 434. In another example, the modification can comprise a 428L (e.g., M428L) and 434S (e.g., N434S) modification; a 428L, 259I (e.g., V259I), and a 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); or a 307 and/or 308 modification (e.g., 308F or 308P).

The term "cell" includes any cell that is suitable for expressing a recombinant nucleic acid sequence. Cells include those of prokaryotes and eukaryotes (single-cell or multiple-cell), bacterial cells (e.g., strains of E. coli, Bacillus spp., Streptomyces spp., etc.), mycobacteria cells, fungal cells, yeast cells (e.g., S. cerevisiae, S. pombe, P. pastoris, P. methanolica, etc.), plant cells, insect cells (e.g., SF-9, SF-21, baculovirus-infected insect cells, Trichoplusiani, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g. a retinal cell that expresses a viral gene (e.g., a PER.C6™ cell).

The term "fatty acid ester" means any organic compound that contains a fatty acid chain linked to a head group via an ester bond. An ester bond is formed when a hydroxyl group (e.g., an alcohol or carboxylic acid) is replaced by an alkoxy group. As used herein, the hydroxyl group can be part of a carboxylic acid, more specifically a fatty acid, and/or an alcohol, such as glycerol, sorbitol, sorbitan, isosorbide, or the like. The alcohol group is generally referred to herein as the head group.

Examples of fatty acid esters generally include phospholipids, lipids (e.g., the head group is glycerol, including monoglycerides, diglycerides, and triglycerides), and surfactants and emulsifiers, including for example polysorbates like polysorbate 20, polysorbate 60, and polysorbate 80, which are non-ionic detergents. Surfactants and emulsifiers are useful as cosolvents and stabilizers. They function by associating with both a hydrophilic surface and a lipophilic surface to maintain dispersion and structural stability of ingredients, like proteins. Surfactants are added to protein formulations primarily to enhance protein stability against mechanical stress, such as air/liquid interface-induced and solid/liquid interface-induced partial unfolding and self-association. Without a surfactant, proteins may in some cases become structurally unstable in solution, and form multimeric aggregates that eventually become subvisible particles.

The term "fatty acid" or "fatty acid chain" means a carboxylic acid having an aliphatic tail. An aliphatic tail is simply a hydrocarbon chain comprising carbon and hydrogen, and in some cases, oxygen, sulfur, nitrogen and/or chlorine substitutions. Aliphatic tails can be saturated (as in saturated fatty acids), which means that all carbon-carbon bonds are single bonds (i.e., alkanes). Aliphatic tails can be unsaturated (as in unsaturated fatty acids), wherein one or more carbon-carbon bonds are double bonds (alkenes), or triple bonds (alkynes).

Fatty acids are generally designated as short-chain fatty acids, which have fewer than six carbons in their aliphatic tails, medium-chain fatty acids having six to twelve carbons, long-chain fatty acids having thirteen to twenty one carbons, and very long chain fatty acids having aliphatic tails of twenty two carbons and longer. As mentioned above, fatty acids are also categorized according to their degree of saturation, which correlates to stiffness and melting point. Common fatty acids include caprylic acid (8 carbons : 0 double bonds; 8:0), capric acid (10:0), lauric acid (12:0), myristic acid (14:0), myristoleic acid (14:1), palmitic acid (16:0), palmitoleic acid (16:1), sapienic acid (16:1), stearic acid (18:0), oleic acid (18:1), elaidic acid (18:1), vaccenic acid (18:1), linoleic acid (18:2), linelaedic acid (18:2), alpha-linolenic acid (18:3), arachidic acid (20:0), arachidonic acid (20:4), eicosapentaenoic acid (20:5), behenic acid (22:0), erucic acid (22:1), docosahexaenoic acid (22:6), lignoceric acid (24:0), and cerotic acid (26:0).

As mentioned above, polysorbates are fatty acid esters useful as non-ionic surfactants and protein stabilizers. Polysorbate 20, polysorbate 40, polysorbate 60, and polysorbate 80 are widely employed in the pharmaceutical, cosmetic, and food industries as stabilizers and emulsifiers. Polysorbate 20 mostly comprises the monolaurate ester of polyoxyethylene (20) sorbitan. Polysorbate 40 mostly comprises the monopalmitate ester of polyoxyethylene (20) sorbitan. Polysorbate 60 mostly comprises the monostearate ester of polyoxyethylene (20) sorbitan. Polysorbate 80 mostly comprises the monooleate ester of polyoxyethylene (20) sorbitan (depicted in FIG. 1).

The quality of commercial grades of polysorbates varies from vendor to vendor. Polysorbates therefore are often mixtures of various chemical entities, consisting mostly of polyoxyethylene (20) sorbitan monoesters (as described above) with, in some cases, isosorbide ester contaminants. They may also include, for example, polyethylene glycol (PEG), intermediate structures, and fatty acid reactants. The head group (in this case polyoxyethylene (20) sorbitan) comprises a sorbitan (a mixture of dehydrated sorbitols, including 1,4-anhydrosorbitol, 1,5-anhydrosorbitol, and 1,4, 3,6-dianhydrosorbitol) substituted at three of its alcohol groups to form ether bonds with three polyoxyethylene groups. The fourth alcohol group is substituted with a fatty acid to form a fatty acid ester.

In some commercially available batches of polysorbates, the polysorbate contains isosorbide monoesters. Isosorbide is a heterocyclic derivative of glucose, also prepared by the dehydration of sorbitol. It is a diol, i.e., having two alcohol groups that can take part in the formation of one or two ester bonds. Thus, for example, some lots of polysorbate 80 can contain significant amounts of isosorbide oleate mono- and di-esters.

In addition to head group variation, preparations of polysorbates contain variable amounts of other fatty acid esters. For example, an analysis of one particular source of polysorbate 80 revealed <5% myristic acid, <16% palmitic acid, >58% oleic acid, <6% stearic acid, and <18% linoleic acid. An analysis of another source of polysorbate 80 revealed about 70% oleic acid, with the remainder being other fatty acid esters and impurities. An analysis of yet another source of polysorbate 80 revealed about 86-87% oleic acid. An analysis of a further, more recently-developed source of polysorbate 80 revealed ≥99% oleic acid.

Non-ionic detergents like polysorbate 20 or polysorbate 80 help stabilize large molecules like antibodies and other proteins, and help prevent the formation of oligomeric complexes or other aggregates. Aggregates can become nanoparticles or subvisible particles in the 10 to 100 micron range or 2 to 100 micron range, and interfere with drug product stability and shelf-life, and may induce immunogenicity. Therefore, the stability of protein formulations depends in some cases upon the stability of the non-ionic detergent additive. However, and as is further discussed herein, polysorbate 20 and polysorbate 80 can, in some instances, contribute to the formation of aggregates, nanoparticles, and subvisible particles.

The phrases "subvisible particle" (SVP) and "subvisible particulate" according to the present disclosure refers to a particle that is not visible to the naked eye, especially in a liquid. In other words, a solution or other liquid containing SVPs, but not visible particles, will not appear cloudy. SVPs generally include those particles 100 microns or less in diameter, but in some cases include particles under 150 microns (Narhi et al., "A critical review of analytical methods for subvisible and visible particles," Curr Pharm Biotechnol 10(4):373-381 (2009)). SVPs may be the result of foreign contaminants, protein aggregation, or aggregation of other components of DP. SVPs may comprise, inter alia, silicone oil droplets (oily droplets), free fatty acids (amorphous particles and/or oily droplets), aggregated protein (amorphous particles), and/or protein/fatty acid complexes (amorphous particles).

SVPs can be detected by any one or more of various methods. The USP standards specify light obscuration and optical microscopy protocols. Other methods include micro-flow image (MFI) analysis, Coulter counting, and submicron particle tracking methods. Several methods of measurement and characterization of SVPs (e.g., light obscuration, flow microscopy, the electrical sensing zone method, and flow cytometry, are discussed in, for example, Narhi et al., "Subvisible (2-100 µm) Particle Analysis During Biotherapeutic Drug Product Development: Part 1, Considerations and Strategy," J. Pharma. Sci. 104:1899-1908 (2015).

Light obscuration is criticized for underestimating protein aggregates and other amorphous structures. Flow image analysis, such as micro-flow imaging (MFI) (Brightwell Technologies, Ottawa, Ontario), is a more sensitive method of detecting the irregularly shaped, fragile, and transparent proteinaceous SVPs, and of differentiating those types of particles from silicone micro-droplets, air bubbles, and other foreign contaminants (Sharma et al., "Micro-flow imaging: Flow microscopy applied to sub-visible particulate analysis in protein formulations," AAPS J. 12(3): 455-464 (2010)). In general, because SVP measurement and characterization by light obscuration analysis is less sensitive than MFI, particle counts detected by MFI will tend to be higher than particle counts detected by light obscuration analysis. Briefly, MFI is flow microscopy in which successive bright field images are taken and analyzed in real time. Image analysis algorithms are applied to the images to discriminate air bubbles, silicone oil droplets, and proteinaceous aggregates. Volumes as low as about 250 microliters to as high as tens of milliliters can be analyzed. Depending on the system used, particles in the range of two to 300 microns, or one to 70 microns can be detected. (Id.)

The FDA and other government regulatory agencies have placed limits on the amount of SVPs allowed in parenteral drug formulations. The major articulated concern is the uncertainty surrounding potential immunogenicity and downstream negative effects in the patient receiving the drug (Singh et al., "An industry perspective on the monitoring of subvisible particles as a quality attribute for protein therapeutics," J. Pharma. Sci. 99(8):3302-21 (2010)). For small volume parenteral drugs (e.g., 100 mL or below), the pharmacopeia limits SVPs of greater than or equal to 10 microns to no more than 6,000 SVPs per container, and SVPs of greater than or equal to 25 microns to no more than 600 per container, when determined by light obscuration analysis; and SVPs of greater than or equal to 10 microns to no more than 3,000 SVPs per container, and SVPs of greater than or equal to 25 microns to no more than 300 per container, when determined by the membrane microscopic test. (United States Pharmacopeia and National Formulary (USP 40-NF 28), <787>Subvisible Particulate Matter in Therapeutic Protein Injections.) For ophthalmic drugs, the SVP limits are 50 per mL of 10 microns or greater, 5 per mL of 25 microns or greater, and 2 per mL of 50 microns or greater (Id. at <78922 Particulate Matter in Ophthalmic Solutions). Regulatory agencies are increasingly contemplating that manufacturers establish specifications for SVPs of 2 microns or greater (see Singh et al., "An industry perspective on the monitoring of subvisible particles as a quality attribute for protein therapeutics," J. Pharma. Sci. 99(8):3302-21 (2010)).

The term "esterase" means an enzyme that catalyzes the hydrolysis of an ester bond to create an acid and an alcohol. Esterases are a diverse category of enzymes, including acetyl esterases (e.g., acetylcholinesterase), phosphatases, nucleases, thiolesterases, lipases and other carboxyl ester hydrolases (EC 3.1. As its name implies a carboxyl ester hydrolase (a.k.a. carboxylesterase, carboxylic-ester hydrolase, and EC 3.1.1.1) uses water to hydrolyze a carboxylic ester into an alcohol and a carboxylate. A lipase is a carboxyl ester hydrolase that catalyzes the hydrolysis of lipids, including triglycerides, fats and oils into fatty acids and an alcohol head group. For example, triglycerides are hydrolyzed by lipases like pancreatic lipase to form monoacylglycerol and two fatty acid chains.

Phospholipases are lipases that hydrolyze phospholipids into fatty acids and other products. Phospholipases fall into four broad categories: phospholipase A (including phospholipase A1 and phospholipase A2), phospholipase B, and the phosphodiesterases phosphodiesterase C and phosphodiesterase D. In addition to the canonical phospholipases, phospholipase B-like enzymes, which reside at the lysosome lumen, are thought to be involved in lipid catalysis. For example, phospholipase B-like 2 (PLBL2) is postulated to have esterase activity based upon sequence homology and subcellular localization (Jensen et al., "Biochemical characterization and liposomal localization localization of the mannose-6-phosphate protein p'76," Biochem. J. 402: 449-458 (2007)).

An enzymatic activity associated with the destabilization of polysorbates (including polysorbate 20 and polysorbate 80) has been discovered. That activity was found to be associated with an esterase, such as a polypeptide comprising the amino acid sequences of Table 1. A BLAST search of those peptide sequences revealed identity with a putative phospholipase B-like 2 (PLBL2). PLBL2 is highly conserved in hamster, rat, mice, human and bovine. The applicants envision that PLBL2, which copurifies under certain processes with some classes of proteins-of-interest (POIs) manufactured in a mammalian cell line, has esterase activity responsible for the hydrolysis of polysorbate 20 and 80. Applicants envision that other esterase species, of which PLBL2 is an example, may contribute to polysorbate instability, depending upon the particular protein-of-interest and/or genetic/epigenetic background of the host cell.

Ester hydrolysis of polysorbate 80 was recently reported (see Labrenz, S. R., "Ester hydrolysis of polysorbate 80 in mAb drug product: evidence in support of the hypothesized risk after observation of visible particulate in mAb formulations," J. Pharma. Sci. 103(8):2268-77 (2014)). That paper reported the formation of visible particles in a formulation containing IgG. The author postulated that the colloidal IgG particles formed due to the enzymatic hydrolysis of oleate esters of polysorbate 80. Although no esterase was directly identified, the author speculates that a lipase or tweenase copurified with the IgG, which was responsible for degrading the polysorbate 80. (Id. at 7.) As stated in that paper, the formation of particles due to the presence of polysorbate 80 is a cause of concern, as such particles may affect the stability and efficacy of the IgG drug product.

TABLE 1

| Sequence Identifier | Amino acid Sequence |
|---|---|
| SEQ ID NO: 1 | DLLVAHNTWNSYQNMLR |
| SEQ ID NO: 2 | LIRYNNFLHDPLSLCEACIPKP |
| SEQ ID NO: 3 | SVLLDAASGQLR |
| SEQ ID NO: 4 | DQSLVEDMNSMVR |
| SEQ ID NO: 5 | QFNSGTYNNQWMIVDYK |
| SEQ ID NO: 6 | QGPQEAYPLIAGNNLVFSSY |
| SEQ ID NO: 7 | SMLHMGQPDLWTFSPISVP |
| SEQ ID NO: 8 | YNNFLHDPLSLCEACIPKPNA |
| SEQ ID NO: 9 | LALDGATWADIFK |
| SEQ ID NO: 10 | LSLGSGSCSAIIK |
| SEQ ID NO: 11 | YVQPQGCVLEWIR |
| SEQ ID NO: 12 | RMSMLAASGPTWDQLPPFQ |
| SEQ ID NO: 13 | SFLEINLEWMQR |
| SEQ ID NO: 14 | VLTILEQIPGMVVVADADKTED |
| SEQ ID NO: 15 | VRSVLLDAASGQLR |
| SEQ ID NO: 16 | LTLLQLKGLEDSYEGR |
| SEQ ID NO: 17 | MSMLAASGPTWDQLPPFQ |
| SEQ ID NO: 18 | VTSFSLAKR |
| SEQ ID NO: 19 | QNLDPPVSR |
| SEQ ID NO: 20 | IIKKYQLQFR |
| SEQ ID NO: 21 | AQIFQRDQSLVEDMNSMVR |
| SEQ ID NO: 22 | LIRYNNFLHDPLSLCEACIPKP |
| SEQ ID NO: 23 | SVLLDAASGQLR |
| SEQ ID NO: 24 | DQSLVEDMNSMVR |
| SEQ ID NO: 25 | DLLVAHNTWNSYQNMLR |
| SEQ ID NO: 26 | YNNFLHDPLSLCEACIPKPNA |
| SEQ ID NO: 27 | RMSMLAASGPTWDQLPPFQ |

TABLE 1-continued

| Sequence Identifier | Amino acid Sequence |
|---|---|
| SEQ ID NO: 28 | SMLHMGQPDLWTFSPISVP |
| SEQ ID NO: 29 | MSMLAASGPTWDQLPPFQ |
| SEQ ID NO: 30 | VRSVLLDAASGQLR |
| SEQ ID NO: 31 | QNLDPPVSR |

As used herein, the phrase "percent fatty acid ester hydrolysis" means the molar proportion of fatty acid ester that has been hydrolyzed. Since hydrolysis of a fatty acid ester results in the release of a free fatty acid, the percent fatty acid ester hydrolysis can be determined by measuring the free fatty acid in a sample. Therefore, percent fatty acid ester hydrolysis may be determined by calculating moles of free fatty acid divided by the sum of moles of free fatty acid plus moles of fatty acid ester. In the case of percent hydrolysis of polysorbate 80 or polysorbate 20, that number may be determined by calculating the moles of free fatty acid, and dividing by the total moles of remaining polysorbate plus moles of free fatty acid.

The term "esterase inhibitor" means any chemical entity that reduces, inhibits, or blocks the activity of an esterase. The applicants envision that the inclusion of an esterase inhibitor in a protein formulation containing a fatty acid ester surfactant may help maintain protein stability and help reduce SVP formation. Common esterase inhibitors known in the art include orlistat (tetrahydrolipistatin; an inhibitor of carboxylesterase 2 and lipoprotein lipase), diethylumbelliferyl phosphate (a cholesterol esterase [lipsase A] inhibitor), URB602 ([1-1'-biphenyl]-3-t1-carbamicacid cyclohexyl ester; a monoacylglycerol lipase inhibitor), and 2-butoxyphenylboronic acid (an inhibitor of hormone-sensitive lipase). The inclusion of an esterase inhibitor during purification of a protein of interest or in the final formulation may prevent or slow the hydrolysis of non-ionic detergents like polysorbate 80, which in turn are expected to prevent or reduce subvisible particle formation. However, the inclusion of an esterase inhibitor may also negatively affect the functioning of the active ingredient, or other ingredients, in the final formulation.

The term "buffer" means a buffering solution or a buffering agent that stabilizes the pH of a solution. A buffer generally comprises a weak acid and its conjugate base, or a weak base and its conjugate acid. Buffering of a protein solution at or close to the optimal pH helps to ensure proper protein folding and function. The best buffer can be identified, for example, by measuring the thermodynamic stability (DSC), and high molecular weight variants (SEC) and charge variants (CEX) of the protein (e.g., antibody) solution at various pHs following accelerated storage/incubation. Measuring the circular dichroism of the protein (e.g., antibody) solution at various pHs may also assist in identifying a buffer. Circular dichrosim (CD) is one method used to determine structural changes (unfolding) of a protein (S. Beychok, "Circular dichroism of biological macromolecules," Science 154(3754):1288-99 (1966); Kemmer and Keller, "Nonlinear least-squares data fitting in Excel spreadsheets," Nat Protoc. 5(2):267-81 (2010)). Some proteins possess the ability to act as buffers (i.e., so called "self-buffering") and therefore may not require the addition of an exogenous buffer to maintain stable pH (Gokarn et al., "Self-buffering antibody formulations," J Pharm Sci. 97(8):

3051-66 (2008)). Examples of commonly used buffers are listed in Table 2. For a more complete discussion of buffers in biological solutions, see Irwin H. Segel, Biochemical Calculations ($2^{nd}$ ed. 1976), or Remington, The Science and Practice of Pharmacy 244 (Paul Beringer et al. eds., $21^{st}$ ed. 2006).

TABLE 2

| Buffering Agent | pKa | Useful pH |
|---|---|---|
| Histidine | 1.82, 6.0, 9.17 | 5.5-7.4 |
| Citrate | 3.13, 4.76, 6.40 | 2.1-7.4 |
| Glycine | 2.35, 9.78 | 2.2-3.6, 8.8-10.6 |
| Acetate | 4.8 | 3.8-5.8 |
| Phosphate | 7.2 | 6.2-8.2 |
| Succinate | 4.21, 5.64 | 3.2-6.5 |
| Tris | 8.06 | 7.5-9.0 |
| HEPES | 7.48 | 6.8-8.2 |
| MOPS | 7.20 | 6.5-7.9 |
| PIPES | 6.76 | 6.1-7.5 |

The term "thermal stabilizer" means an excipient or other additive included in a biopharmaceutical formulation to provide protection to the protein against thermal degradation, denaturation, and erosion of biological activity. Generally, a thermal stabilizer helps maintain the protein (e.g., antibody) in its native conformation and prevent aggregation under conditions of thermal stress. Thermal stress may occur from freeze-thaw cycling, exposure to high temperatures, or extensive storage time. Thermal stabilizers include sugars and other carbohydrates, sugar alcohols and polyols like polyethylene glycol, and amino acids like glycine. Examples of sugars or sugar alcohols useful as a thermal stabilizer include sucrose, trehalose and mannitol.

The term "hydrophobic interaction media" means a combination of a support structure and a hydrophobic moiety, wherein the hydrophobic moiety is affixed to the support structure. The media can be in the form of chromatography media, e.g., beads or other particles held in a packed bed column format, in the form of a membrane, or in any format that can accommodate a liquid comprising a protein of interest and contaminants. Thus, support structures include agarose beads (e.g., sepharose), silica beads, cellulosic membranes, cellulosic beads, hydrophilic polymer beads, and the like. The hydrophobic moiety binds to hydrophobic molecules and hydrophobic surfaces of proteins. The degree of hydrophobicity of the media can be controlled by selecting the hydrophobic moiety. Hydrophobic interaction media is employed in a process known as hydrophobic interaction chromatography (HIC) and is used to separate proteins of interest from product and process related contaminants. When the protein of interest is manufactured in and/or purified from host cells, the product and process related contaminants are referred to as host cell proteins (HCP). HCPs from Chinese hamster ovary (CHO) cells, a common biotherapeutic manufacturing host cell, can be referred to as CHOPs (Chinese hamster ovary proteins). In some cases, a mixture containing the protein of interest (POI) and HCPs are applied to the HIC media in a buffer designed to promote binding of hydrophobic groups in the POI to the hydrophobic moiety of the HIC medium. The POI sticks to the HIC media by binding the hydrophobic moiety, and some HCPs fail to bind and come out in the wash buffer. The POI is then eluted using a buffer that promotes dissociation of the POI from the HIC hydrophobic moiety, thereby separating the POI from unwanted HCPs.

In some cases, the HIC hydrophobic moiety binds some contaminants such as HCPs, and the POI is collected from the HIC flow-through.

In some cases affinity chromatography designed to bind specific proteins having lipophilic attributes is employed in lieu of or in concert with HIC. Since some esterases, such as lipases in general, or phospholipases in particular, bind to triglycerides or phospholipids, molecules that mimic those lipids may be used to capture esterases. For example, "myristoylated ADP ribosylating factor 1" (a.k.a. "myrARF1") can be used to capture a lipase and allow the POI to remain unbound and flow through.

As used herein, the term "container" is meant to include a primary packaging component such as a syringe (as in a pre-filled syringe), a vial (for example a 2.5 mL glass vial for storing a biopharmaceutical formulation), or any vessel or means to contain a soild, liquid or gaseous substance. Here, the term "container" is used to refer inter alfa to the vessel containing a biopharmaceutical formulation, as that term is used by the FDA and USP in its guidance on limitations for subvisible particles (United States Pharmacopeia and National Formulary (USP 40-NF 28), <787>Subvisible Particulate Matter in Therapeutic Protein Injections).

The terms "composition," "formulation," and "formulated drug substance" (FDS) as used in the present disclosure refer to a combination of two or more pharmaceutical ingredients for inclusion in a drug product. A composition, formulation, or FDS may be, for example, a liquid composition including an active pharmaceutical ingredient, such as an antibody, and an excipient, such as a stabilizer or surfactant. A composition, formulation, or FDS may include multiple excipients. A composition, formulation, or FDS may also include other constituents, such as proteins co-purified with an antibody.

The term "drug product" (DP) as used in the present disclosure refers to a dosage form comprising an amount of a FDS for packaging, shipment, or administration. For example, a drug product may be a pre-filled syringe holding a volume of FDS for administration to a patient.

As has been discussed above, it is hypothesized that HCPs such as PLBL2, which copurify with some POIs, exhibit esterase-like activity on fatty acid esters in polysorbates that are used in formulations and drug products with those POIs. This esterase-like behavior is thought to result in formation of free fatty acids that then may aggregate to form SVPs. While HIC and/or affinity chromatography may be used to purify a POI and remove HCPs from a drug product or formulation, thus reducing esterase-like behavior on fatty acid esters, the addition of a HIC or affinity chromatography step requires adding equipment (e.g., hydrophobic interaction media), materials, preparation, protocol, and protocol validation to a drug product's manufacturing process, meaning added time, resources, experimentation, and costs. Therefore, it is desirable to have an alternative method of decreasing SVP formation in formulations and drug products including a POI, a polysorbate, and a co-purified HCP.

It has been found that FDS and drug products which include a POI and a polysorbate 80 having a high percentage (e.g., >98%) of oleic acid ester content exhibit less measurable formation of SVPs over time than, e.g., FDS and drug products including polysorbate 80 having a relatively lower percentage (e.g., 70% or 86-87%) of oleic acid ester content. This is the case even when the POI is not subjected to HIC or affinity chromatography to remove HCPs that have esterase-like behavior on fatty acid esters.

Embodiments of the present disclosure relate to FDS and drug products including a POI (such as an antibody) and polysorbate 80 having >98% oleic acid ester content, where the POI has not been subjected to a HIC or affinity chromatography step to remove HCPs having esterase-like behavior. In some embodiments of the present disclosure, FDS and drug products exhibit formation of fewer than 3,000 particles having a diameter of 10 μm or larger when stored in a container at a temperature of, e.g., 5° C. for at least 6 months. In some embodiments, FDS and drug products exhibit formation of fewer than 2,000, 1,500, 1,000, 800, 600, 500, 400, 300, 290, 275, 270, or 250 particles having a diameter of 10 μm or larger when stored in a container at a temperature of, e.g., 5° C. for at least 6 months. In some aspects, embodiments of the present disclosure relate to methods of preparing such FDS and drug products.

In embodiments of the present disclosure, the FDS or drug product includes a POI. In some embodiments, the POI is an antibody, such as a human monoclonal antibody. In some embodiments, the POI is an immunoglobulin, such as IgG. In some embodiments, the protein is an IgG 1, an IgG 2, an IgG 3, or an IgG 4. In some embodiments, the FDS or drug product includes more than one POI (e.g., the FDS or drug product includes a co-formulation of two or more POIs).

In embodiments of the present disclosure, the POI may have been purified by a purification step known in the art. For example, if the POI is an immunoglobulin, it may have been purified using a Protein A or Protein G affinity purification step. In some embodiments, one or more HCPs or other impurities may have been copurified with the POI during this purification step. For example, in some embodiments, the FDS or drug product includes an esterase copurified with the POI. In some embodiments, the esterase is a phospholipase B-like protein, such as PLBL2.

In embodiments of the present disclosure, the concentration of the POI in the FDS or drug product may range from about 40 mg/mL to about 250 mg/mL, such as, for example, between about 50 mg/mL and about 160 mg/mL, between about 80 mg/mL and 100 mg/mL, between about 100 mg/mL and 160 mg/mL, between about 125 mg/mL and 155 mg/mL.

In embodiments, the FDS or drug product includes an amount of a surfactant or stabilizer. In some embodiments, the surfactant or stabilizer is a polysorbate 80 including a mix of fatty acid esters, and which has at least a 97%, 98%, or 99% content of oleic acid esters. In some embodiments, the surfactant or stabilizer is polysorbate 80 including a mix of fatty acid esters, and which has a >98% content of oleic acid esters. In further embodiments, the surfactant or stabilizer is a polysorbate 80 including a mix of fatty acid esters, and which has a >99% content of oleic acid esters. In embodiments, a concentration of the surfactant or stabilizer in the FDS or drug product is between 0.005% and 1.00% (w/v), such as 0.5% (w/v).

In some embodiments, a volume of the FDS or drug product is between about 0.25 mL and 3 mL, such as 0.25 mL, 0.5 mL, 1 mL, 1.5 mL, 2 mL, 2.25 mL, 2.5 mL, or 3 mL. In some embodiments, the drug product includes a volume of the FDS packaged in a container.

In some embodiments, the FDS or drug product includes additional excipients, such as a buffer, a thermal stabilizer, or an esterase inhibitor.

In some embodiments, the FDS or drug product is stored at a temperature of about 2-8° C. for at least 6 months. In other embodiments, the FDS or drug product is stored at a temperature of, e.g., about 5° C., 15° C., 22° C., 24° C., or 30-50° C., such as about 35° C., 40° C., 45° C., or 50° C.

In some embodiments, the FDS or drug product is stored for up to, e.g., 2-4 weeks, 2 months, 3 months, 4 months, 5 months, 6 months, 12 months, 18 months, 24 months, or 36 months. For example, in some embodiments, the FDS or drug product is stored at a temperature of about 5° C. for up to 24 months. In other embodiments, the FDS or drug product is stored at a temperature of about 30-50° C. for up to 5 months.

EXAMPLES

Example 1

The storage stability of an IgG4 antibody drug product prone to forming free fatty acid-based subvisible particulates due to degradation of polysorbate by a co-purified host cell protein (HCP) lipase was evaluated in different DP samples. Each DP sample had a volume of 2.136 mL, contained the same concentration of the IgG4 antibody (150 mg/mL), and 0.2% (w/v) of one of several lots of PS80. Each lot of PS80 lots had one of three different percentage contents of oleic acid ester (70%, 87%, and ≥99%). The table below summarizes the percentage content of oleic acid ester in the PS80 in each FDS sample.

TABLE 3

| Name | % content of oleic acid ester in PS80 (Lot) |
| --- | --- |
| DP A | 87% |
| DP B | ≥99% (Lot 1) |
| DP C | ≥99% (Lot 2) |
| DP D | 70% (Lot 1) |
| DP E | 70% (Lot 2) |
| DP F | 70% (Lot 3) |

The DP samples were stored at 2-8° C. in glass pre-filled syringes for up to 24 months. Particulates were measured in each DP sample every six months for a total of 24 months, by both the microscopic method and micro-flow imaging (MFI).

Figure 2:
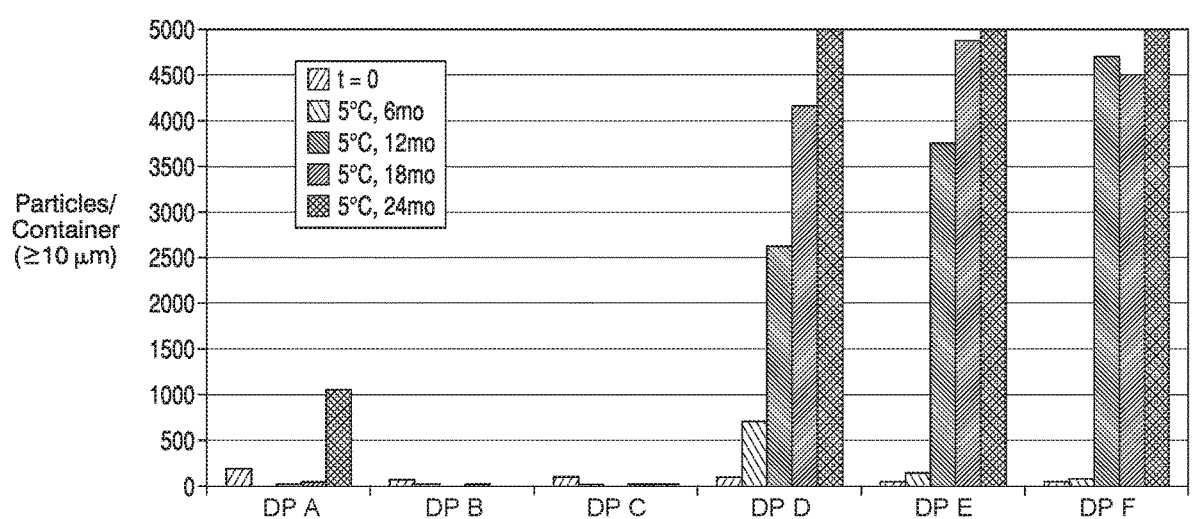
FIG. 2 is a chart depicting the number of subvisible particulates ($\geq 10$ μm) measured by the membrane microscopic method, in protein drug products comprising various types of polysorbate 80.
Figure 3:
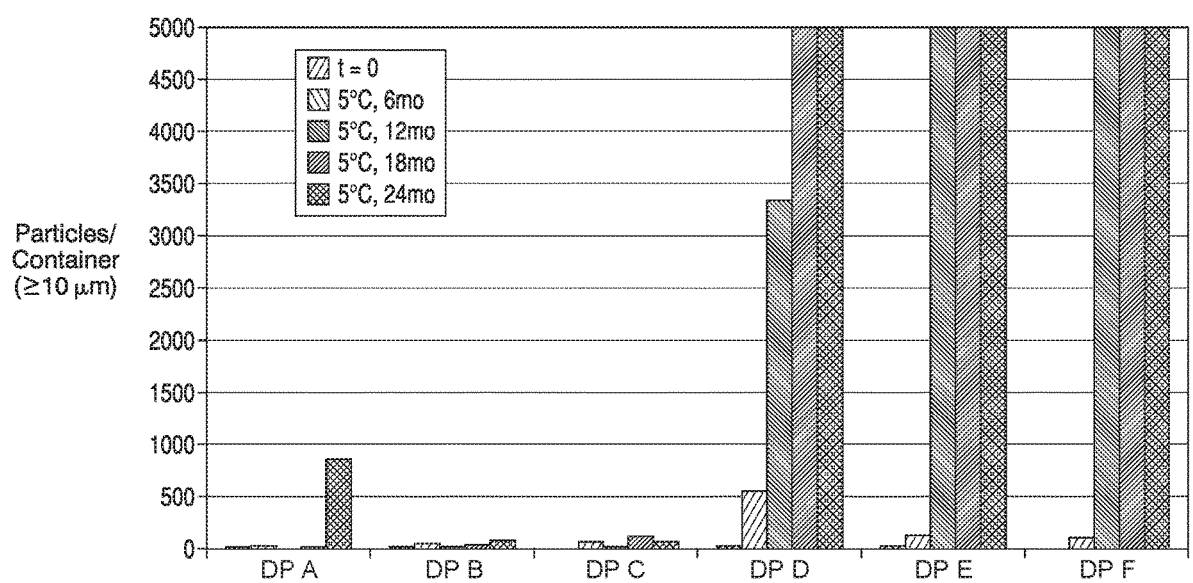
FIG. 3 is a chart depicting the number of subvisible particulates ($\geq 10$ μm) measured by micro-flow imaging (MFI), in protein drug products comprising various types of polysorbate 80.

FIG. 2 shows, in chart form, the number of SVPs per container having a diameter of ≥10 μm, as measured by the microscopic method. FIG. 3 shows, in chart form, the number of SVPs per container having a diameter of ≥10 μm, as measured by MFI. As is shown in FIGS. 2 and 3, DP B and DP C (the two DP samples containing PS80 having a ≥99% content of oleic acid esters) displayed the lowest numbers of SVPs across the full 24-month period, as measured by both microscopy (FIG. 2) and MFI (FIG. 3). DP A, containing PS80 having an 87% content of oleic acid esters, displayed the next lowest number of subvisible particulates across the 24-month period (in particular, showing between 800 and 1200 particles by 24 months). DPs D, E, and F all showed well over 3000 particles per container (as measured by both methods) by at least the 18-month mark.

It was hypothesized that the lower numbers of particles in DPs A, B, and C (as compared to the more numerous particles in DPs D, E, and F) were a result of the use of PS80 having a higher percentage content of oleic acid (or long-chain fatty acid) esters. Oleic acid is a longer chain fatty acid, with one unsaturated bond (see FIG. 1). Therefore, it has a sub-ambient melting temperature of about 13° C. A precursor to subvisible and visible free fatty acid (FFA) particulate formation is the agglomeration of individual FFA chains into aggregates, which then precipitate in the form of particles. Oleic acid may be generated during storage of the formulations at 5° C. by, e.g., enzymatic hydrolysis of the fatty acid esters in polysorbate 80. This oleic acid may form SVPs, but due to its low melting temperature, such particles are more likely to exist as an oily liquid in protein formulations at room temperature (about 22° C.) where analysis is performed, and therefore does not persist as subvisible particulates at room temperature. As a contrast, higher amounts of non-oleic acid ester content in the formulation will lead to formation of their corresponding FFA upon hydrolysis, and due to their higher melting temperatures the subvisible and visible amorphous particulates thus formed persist at ambient temperature during analysis.

Additionally, oleic acid esters are better solubilizing/stabilizing agents than esters of shorter chain fatty acids due to their (oleic acid esters') higher hydrophobicity, which enables oleic acid esters to solubilize free fatty acid and protein particulates thereby maintaining product stability.

Therefore, polysorbate 80 with higher contents of oleic acid esters (>98%) can provide improved stability to protein formulations and drug products as compared to polysorbate 80 with lower contents of oleic acid esters.

Example 2

Figure 4:
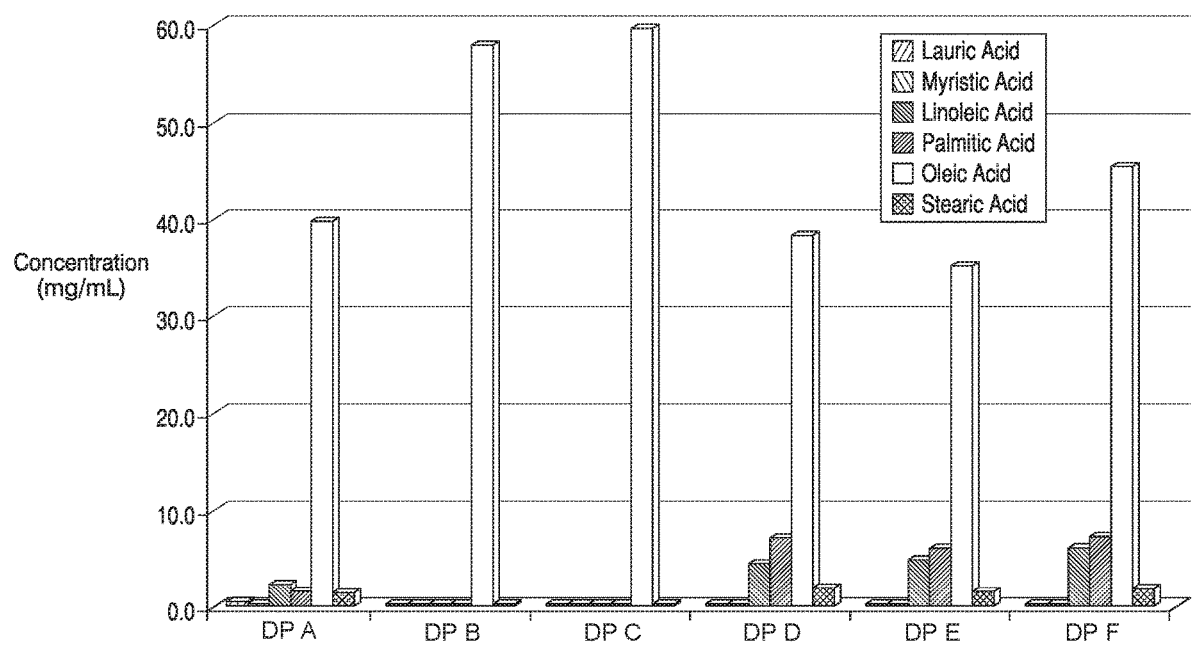
FIG. 4 is a chart depicting the measured concentration of free fatty acids in protein drug products comprising various types of polysorbate 80.

A concentration of each type of free fatty acid (in micrograms/mL) in each sample DP (DP A-F) was evaluated after storage of the samples at 5° C. for 18 months. Sample DP A-F were prepared as described in Example 1. Free fatty acid concentrations were measured at 18 months by LC-MS. FIG. 4 displays the results in chart form. As depicted, DPs B and C (the two DP samples containing PS80 having a ≥99% content of oleic acid esters) displayed the highest concentration of oleic acid, and the lowest concentrations of other FFAs. This indicates the homogeneity of the FFAs (i.e., oleic acids) in DPs B and C.

What is claimed is:

1. A method of reducing subvisible and visible particle formation in a drug product, the method comprising:
   including at least 100 mg/mL of an IgG antibody in the drug product;
   including a mixture of fatty acid esters of polyoxyethylene sorbitan in the drug product, the polyoxyethylene sorbitan having a content of greater than 98% oleic acid esters, wherein the mixture of fatty acid esters of polyoxyethylene sorbitan is present in an amount ranging from 0.005% to 1.00%, relative to the total weight of the drug product; and
   storing the drug product at a temperature of between 2° C. and 8° C. for between 6 months and 24 months,
   wherein after the storing step, fewer than 3000 particles having a diameter of 10 microns or greater are detectable in the drug product as detected by one of flow imaging microscopy or membrane microscopy.

2. The method of claim 1, further comprising adding an agent to reduce viscosity to the drug product.

3. The method of claim 1, wherein the IgG antibody is an IgG4 antibody.

4. The method of claim 1, wherein the IgG antibody is capable of being co-purified with a lipase, and the drug product includes the lipase.

5. The method of claim 1, wherein the IgG antibody has been purified using an affinity purification step prior to inclusion in the drug product.

6. The method of claim 1, wherein the step of including at least 100 mg/mL of the IgG antibody in the drug product comprises including at least 150 mg/mL of the IgG antibody in the drug product.

7. The method of claim 1, wherein the IgG antibody has not been purified using hydrophobic interaction chromatography (HIC) prior to inclusion in the drug product.

8. The method of claim 1, wherein the IgG antibody is an IgG4 antibody, and the drug product includes phospholipase B-like 2 protein.

9. The method of claim 1, further comprising purifying the IgG antibody using a Protein A purification step before including the IgG antibody in the drug product.

10. The method of claim 1, wherein the content of oleic acid esters in the polyoxyethylene sorbitan is at least 99%.

11. The method of claim 1, wherein the drug product further includes an esterase.

12. A drug product prepared according to the method of claim 1.

13. The method of claim 1, wherein the content of oleic acid esters in the mixture is determined by one of gas-liquid chromatography, liquid chromatography, a colorimetric assay, or a fluorometric assay.

14. The method of claim 1, wherein the drug product is configured for parenteral administration.

15. A method of reducing particulate formation in a drug product including an IgG antibody and an esterase, the method comprising:
    including in the drug product a mixture of polyoxyethylene sorbitan fatty acid esters, the polyoxyethylene sorbitan having a content of oleic acid esters greater than 98% wherein the mixture of fatty acid esters of polyoxyethylene sorbitan is present in an amount ranging from 0.005% to 1%, relative to the total weigh of the drug product, and
    storing the drug product at a temperature of between 2° C. and 8° C. for between 6 months and 24 months,
    wherein the method does not include purifying the IgG antibody using hydrophobic interaction chromatography, and
    wherein after the storing step, fewer than 3000 particles having a diameter of 10 microns or greater are detectable in the drug product as detected by one of flow imaging microscopy or membrane microscopy.

16. The method of claim 15, wherein the IgG antibody is an IgG4 antibody and the esterase is a phospholipase B-like 2 protein.

17. The method of claim 1, wherein a volume of the drug product is between about 0.25 mL and 3 mL.

18. The method of claim 1, wherein the mixture of fatty acid esters of polyoxyethylene sorbitan is present in an amount of 0.5% relative to the total weight of the drug product.

19. The method of claim 1, wherein the mixture of fatty acid esters of polyoxyethylene sorbitan is present in an amount ranging from 0.5% to 1.00%, relative to the total weight of the drug product.

20. The method of claim 15, wherein a volume of the drug product is between about 0.25 mL and 3 mL.

21. The method of claim 15, wherein the mixture of fatty acid esters of polyoxyethylene sorbitan is present in an amount ranging from 0.5% to 1.00%, relative to the total weight of the drug product.

* * * * *

UNITED STATES PATENT AND TRADEMARK OFFICE
CERTIFICATE OF CORRECTION

| | | |
|---|---|---|
| PATENT NO. | : 12,042,538 B2 | Page 1 of 1 |
| APPLICATION NO. | : 16/100369 | |
| DATED | : July 23, 2024 | |
| INVENTOR(S) | : Mayank Patel et al. | |

It is certified that error appears in the above-identified patent and that said Letters Patent is hereby corrected as shown below:

On the Title Page

Column 2, item (56) under Other Publications, Line 9, delete "0" and insert --Carpenter--.

Column 2, item (56) under Other Publications, Line 10, delete "Gapes" and insert --Gaps--.

Signed and Sealed this
Seventeenth Day of September, 2024

Katherine Kelly Vidal
*Director of the United States Patent and Trademark Office*

SEQUENCE LISTING

```
<160> NUMBER OF SEQ ID NOS: 31

<210> SEQ ID NO 1
<211> LENGTH: 17
<212> TYPE: PRT
<213> ORGANISM: Cricetulus griseus

<400> SEQUENCE: 1

Asp Leu Leu Val Ala His Asn Thr Trp Asn Ser Tyr Gln Asn Met Leu
1               5                   10                  15

Arg

<210> SEQ ID NO 2
<211> LENGTH: 22
<212> TYPE: PRT
<213> ORGANISM: Cricetulus griseus

<400> SEQUENCE: 2

Leu Ile Arg Tyr Asn Asn Phe Leu His Asp Pro Leu Ser Leu Cys Glu
1               5                   10                  15

Ala Cys Ile Pro Lys Pro
            20

<210> SEQ ID NO 3
<211> LENGTH: 12
<212> TYPE: PRT
<213> ORGANISM: Cricetulus griseus

<400> SEQUENCE: 3

Ser Val Leu Leu Asp Ala Ala Ser Gly Gln Leu Arg
1               5                   10

<210> SEQ ID NO 4
<211> LENGTH: 13
<212> TYPE: PRT
<213> ORGANISM: Cricetulus griseus

<400> SEQUENCE: 4

Asp Gln Ser Leu Val Glu Asp Met Asn Ser Met Val Arg
1               5                   10

<210> SEQ ID NO 5
<211> LENGTH: 17
<212> TYPE: PRT
<213> ORGANISM: Cricetulus griseus
```

-continued

<400> SEQUENCE: 5

Gln Phe Asn Ser Gly Thr Tyr Asn Asn Gln Trp Met Ile Val Asp Tyr
1               5                   10                  15

Lys

<210> SEQ ID NO 6
<211> LENGTH: 20
<212> TYPE: PRT
<213> ORGANISM: Cricetulus griseus

<400> SEQUENCE: 6

Gln Gly Pro Gln Glu Ala Tyr Pro Leu Ile Ala Gly Asn Asn Leu Val
1               5                   10                  15

Phe Ser Ser Tyr
            20

<210> SEQ ID NO 7
<211> LENGTH: 19
<212> TYPE: PRT
<213> ORGANISM: Cricetulus griseus

<400> SEQUENCE: 7

Ser Met Leu His Met Gly Gln Pro Asp Leu Trp Thr Phe Ser Pro Ile
1               5                   10                  15

Ser Val Pro

<210> SEQ ID NO 8
<211> LENGTH: 21
<212> TYPE: PRT
<213> ORGANISM: Cricetulus griseus

<400> SEQUENCE: 8

Tyr Asn Asn Phe Leu His Asp Pro Leu Ser Leu Cys Glu Ala Cys Ile
1               5                   10                  15

Pro Lys Pro Asn Ala
            20

<210> SEQ ID NO 9
<211> LENGTH: 13
<212> TYPE: PRT
<213> ORGANISM: Cricetulus griseus

<400> SEQUENCE: 9

Leu Ala Leu Asp Gly Ala Thr Trp Ala Asp Ile Phe Lys
1               5                   10

<210> SEQ ID NO 10
<211> LENGTH: 13
<212> TYPE: PRT
<213> ORGANISM: Cricetulus griseus

<400> SEQUENCE: 10

Leu Ser Leu Gly Ser Gly Ser Cys Ser Ala Ile Ile Lys
1               5                   10

<210> SEQ ID NO 11
<211> LENGTH: 13
<212> TYPE: PRT
<213> ORGANISM: Cricetulus griseus

<400> SEQUENCE: 11

```
Tyr Val Gln Pro Gln Gly Cys Val Leu Glu Trp Ile Arg
1               5                   10
```

<210> SEQ ID NO 12
<211> LENGTH: 19
<212> TYPE: PRT
<213> ORGANISM: Cricetulus griseus

<400> SEQUENCE: 12

```
Arg Met Ser Met Leu Ala Ala Ser Gly Pro Thr Trp Asp Gln Leu Pro
1               5                   10                  15

Pro Phe Gln
```

<210> SEQ ID NO 13
<211> LENGTH: 12
<212> TYPE: PRT
<213> ORGANISM: Cricetulus griseus

<400> SEQUENCE: 13

```
Ser Phe Leu Glu Ile Asn Leu Glu Trp Met Gln Arg
1               5                   10
```

<210> SEQ ID NO 14
<211> LENGTH: 22
<212> TYPE: PRT
<213> ORGANISM: Cricetulus griseus

<400> SEQUENCE: 14

```
Val Leu Thr Ile Leu Glu Gln Ile Pro Gly Met Val Val Ala Asp
1               5                   10                  15

Ala Asp Lys Thr Glu Asp
            20
```

<210> SEQ ID NO 15
<211> LENGTH: 14
<212> TYPE: PRT
<213> ORGANISM: Cricetulus griseus

<400> SEQUENCE: 15

```
Val Arg Ser Val Leu Leu Asp Ala Ala Ser Gly Gln Leu Arg
1               5                   10
```

<210> SEQ ID NO 16
<211> LENGTH: 16
<212> TYPE: PRT
<213> ORGANISM: Cricetulus griseus

<400> SEQUENCE: 16

```
Leu Thr Leu Leu Gln Leu Lys Gly Leu Glu Asp Ser Tyr Glu Gly Arg
1               5                   10                  15
```

<210> SEQ ID NO 17
<211> LENGTH: 18
<212> TYPE: PRT
<213> ORGANISM: Cricetulus griseus

<400> SEQUENCE: 17

```
Met Ser Met Leu Ala Ala Ser Gly Pro Thr Trp Asp Gln Leu Pro Pro
1               5                   10                  15

Phe Gln
```

<210> SEQ ID NO 18
<211> LENGTH: 9

```
<212> TYPE: PRT
<213> ORGANISM: Cricetulus griseus

<400> SEQUENCE: 18

Val Thr Ser Phe Ser Leu Ala Lys Arg
1               5

<210> SEQ ID NO 19
<211> LENGTH: 9
<212> TYPE: PRT
<213> ORGANISM: Cricetulus griseus

<400> SEQUENCE: 19

Gln Asn Leu Asp Pro Pro Val Ser Arg
1               5

<210> SEQ ID NO 20
<211> LENGTH: 10
<212> TYPE: PRT
<213> ORGANISM: Cricetulus griseus

<400> SEQUENCE: 20

Ile Ile Lys Lys Tyr Gln Leu Gln Phe Arg
1               5                   10

<210> SEQ ID NO 21
<211> LENGTH: 19
<212> TYPE: PRT
<213> ORGANISM: Cricetulus griseus

<400> SEQUENCE: 21

Ala Gln Ile Phe Gln Arg Asp Gln Ser Leu Val Glu Asp Met Asn Ser
1               5                   10                  15

Met Val Arg

<210> SEQ ID NO 22
<211> LENGTH: 22
<212> TYPE: PRT
<213> ORGANISM: Cricetulus griseus

<400> SEQUENCE: 22

Leu Ile Arg Tyr Asn Asn Phe Leu His Asp Pro Leu Ser Leu Cys Glu
1               5                   10                  15

Ala Cys Ile Pro Lys Pro
            20

<210> SEQ ID NO 23
<211> LENGTH: 12
<212> TYPE: PRT
<213> ORGANISM: Cricetulus griseus

<400> SEQUENCE: 23

Ser Val Leu Leu Asp Ala Ala Ser Gly Gln Leu Arg
1               5                   10

<210> SEQ ID NO 24
<211> LENGTH: 13
<212> TYPE: PRT
<213> ORGANISM: Cricetulus griseus

<400> SEQUENCE: 24

Asp Gln Ser Leu Val Glu Asp Met Asn Ser Met Val Arg
1               5                   10
```

<210> SEQ ID NO 25
<211> LENGTH: 17
<212> TYPE: PRT
<213> ORGANISM: Cricetulus griseus

<400> SEQUENCE: 25

Asp Leu Leu Val Ala His Asn Thr Trp Asn Ser Tyr Gln Asn Met Leu
1               5                   10                  15

Arg

<210> SEQ ID NO 26
<211> LENGTH: 21
<212> TYPE: PRT
<213> ORGANISM: Cricetulus griseus

<400> SEQUENCE: 26

Tyr Asn Asn Phe Leu His Asp Pro Leu Ser Leu Cys Glu Ala Cys Ile
1               5                   10                  15

Pro Lys Pro Asn Ala
            20

<210> SEQ ID NO 27
<211> LENGTH: 19
<212> TYPE: PRT
<213> ORGANISM: Cricetulus griseus

<400> SEQUENCE: 27

Arg Met Ser Met Leu Ala Ala Ser Gly Pro Thr Trp Asp Gln Leu Pro
1               5                   10                  15

Pro Phe Gln

<210> SEQ ID NO 28
<211> LENGTH: 19
<212> TYPE: PRT
<213> ORGANISM: Cricetulus griseus

<400> SEQUENCE: 28

Ser Met Leu His Met Gly Gln Pro Asp Leu Trp Thr Phe Ser Pro Ile
1               5                   10                  15

Ser Val Pro

<210> SEQ ID NO 29
<211> LENGTH: 18
<212> TYPE: PRT
<213> ORGANISM: Cricetulus griseus

<400> SEQUENCE: 29

Met Ser Met Leu Ala Ala Ser Gly Pro Thr Trp Asp Gln Leu Pro Pro
1               5                   10                  15

Phe Gln

<210> SEQ ID NO 30
<211> LENGTH: 14
<212> TYPE: PRT
<213> ORGANISM: Cricetulus griseus

<400> SEQUENCE: 30

Val Arg Ser Val Leu Leu Asp Ala Ala Ser Gly Gln Leu Arg
1               5                   10

<210> SEQ ID NO 31

```
<211> LENGTH: 9
<212> TYPE: PRT
<213> ORGANISM: Cricetulus griseus

<400> SEQUENCE: 31

Gln Asn Leu Asp Pro Pro Val Ser Arg
1               5
```